US00PP24089P3

(12) United States Plant Patent
Olesen

(10) Patent No.: US PP24,089 P3
(45) Date of Patent: Dec. 17, 2013

(54) CLIMBING ROSE PLANT NAMED 'POULCY018'

(50) Latin Name: ***Rosa* hybrid**
Varietal Denomination: Poulcy018

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 112 days.

(21) Appl. No.: 13/317,258

(22) Filed: Oct. 13, 2011

(65) Prior Publication Data

US 2013/0097742 P1 Apr. 18, 2013

(51) Int. Cl.
*A01H 5/00* (2006.01)

(52) U.S. Cl.
USPC ..... Plt./112

(58) Field of Classification Search
USPC ..... Plt./112, 111, 109
See application file for complete search history.

*Primary Examiner* — June Hwu

(57) ABSTRACT

A new garden rose plant of the climbing class which has abundant, yellow-orange flowers and attractive foliage. This new and distinct variety has shown to be uniform and stable in the resulting generations from asexual propagation.

4 Drawing Sheets

Botanical designation: *Rosa* hybrid.
Variety denomination: 'Poulcy018'.

SUMMARY OF THE INVENTION

The present invention constitutes a new and distinct variety of climbing garden rose plant which originated from a controlled crossing between the female seed parent, an unnamed seedling, and the male pollen parent, an unnamed seedling.

The two parents were crossed during the summer of 2000 and the resulting seeds were planted in a controlled environment in Fredensborg, Denmark. The new variety, named 'Poulcy018', originated as a single seedling from the stated cross.

The new variety may be distinguished from its female seed parent primarily by flower color. The seed parent has golden amber flowers while the new variety has yellow-orange blended flowers.

The new variety may be distinguished from its male pollen parent primarily by growth habit. The male pollen parent is bushy and upright while the new variety is arching.

The objective of the hybridization of this rose variety was to create a new and distinct variety for garden use with unique qualities, such as:

1. Uniform and abundant yellow-orange flowers;
2. Vigorous, but compact growth when propagated both as a budded rose and on its own roots;
3. Exceptional disease resistance.
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy018' from all other varieties of which we are aware.

As part of the rose development program, Mogens N. Olesen germinated the seeds from the aforementioned hybridization during winter of 2000 and conducted evaluations on the resulting seedlings in a controlled environment in Fredensborg, Denmark. 'Poulcy018' was selected in the spring of 2001 by the inventor as a single plant from the progeny of the aforementioned hybridization.

Asexual reproduction of 'Poulcy018' by traditional budding and rooted cuttings was first done by Mogens N. Olesen in the nursery in Fredensborg, Denmark in July, 2001. This initial and other subsequent asexual propagations conducted in controlled environments have demonstrated that the characteristics of 'Poulcy018' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcy018'. Plants photographed are 3 years of age. Specifically illustrated in the drawing are.

DETAILED DESCRIPTION OF THE VARIETY

Figure 1:
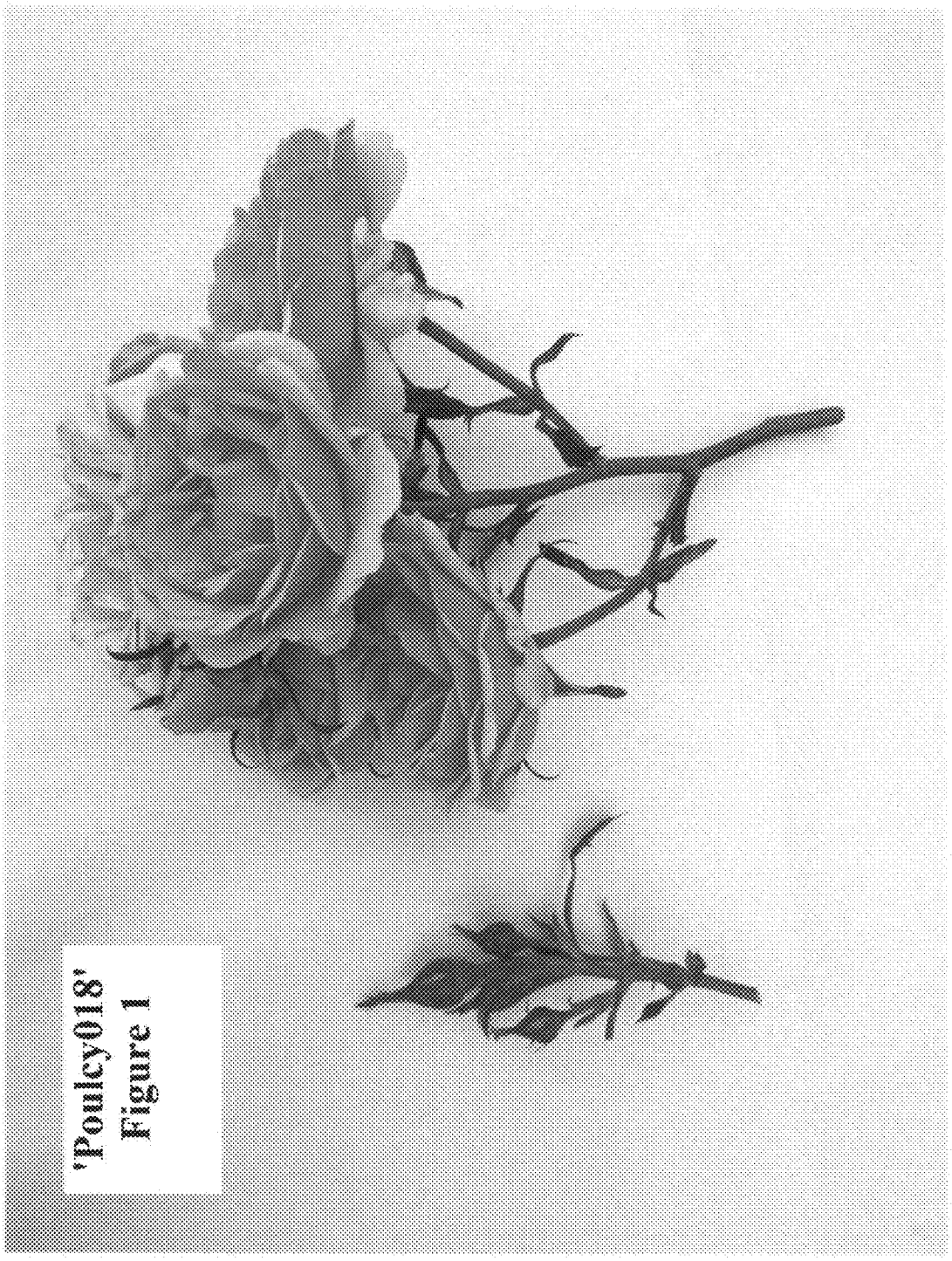
FIG. 1; Cluster of open flowers and flower buds.
Figure 2:
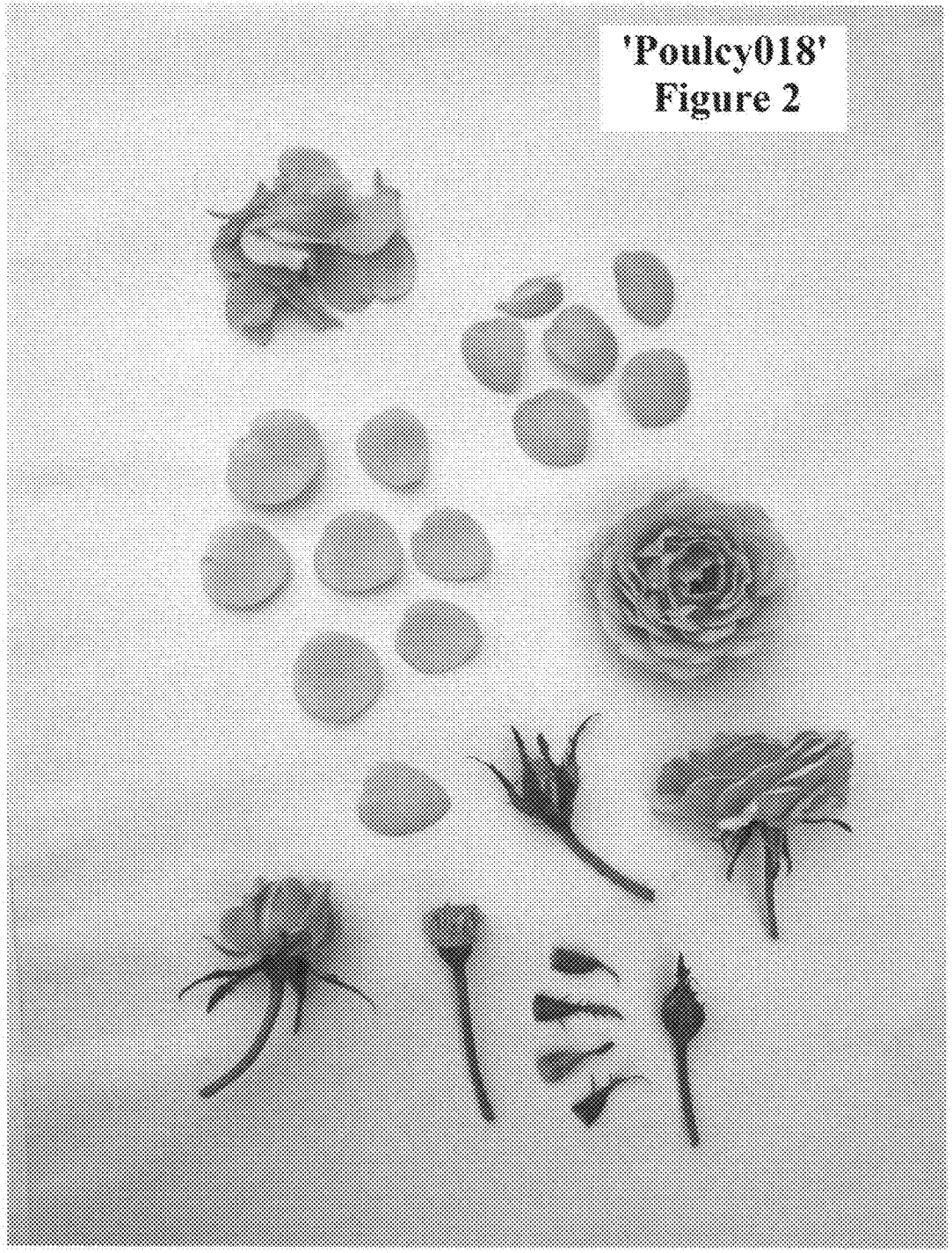
FIG. 2; Open flowers, flower buds, petals and sepals detached.
Figure 3:
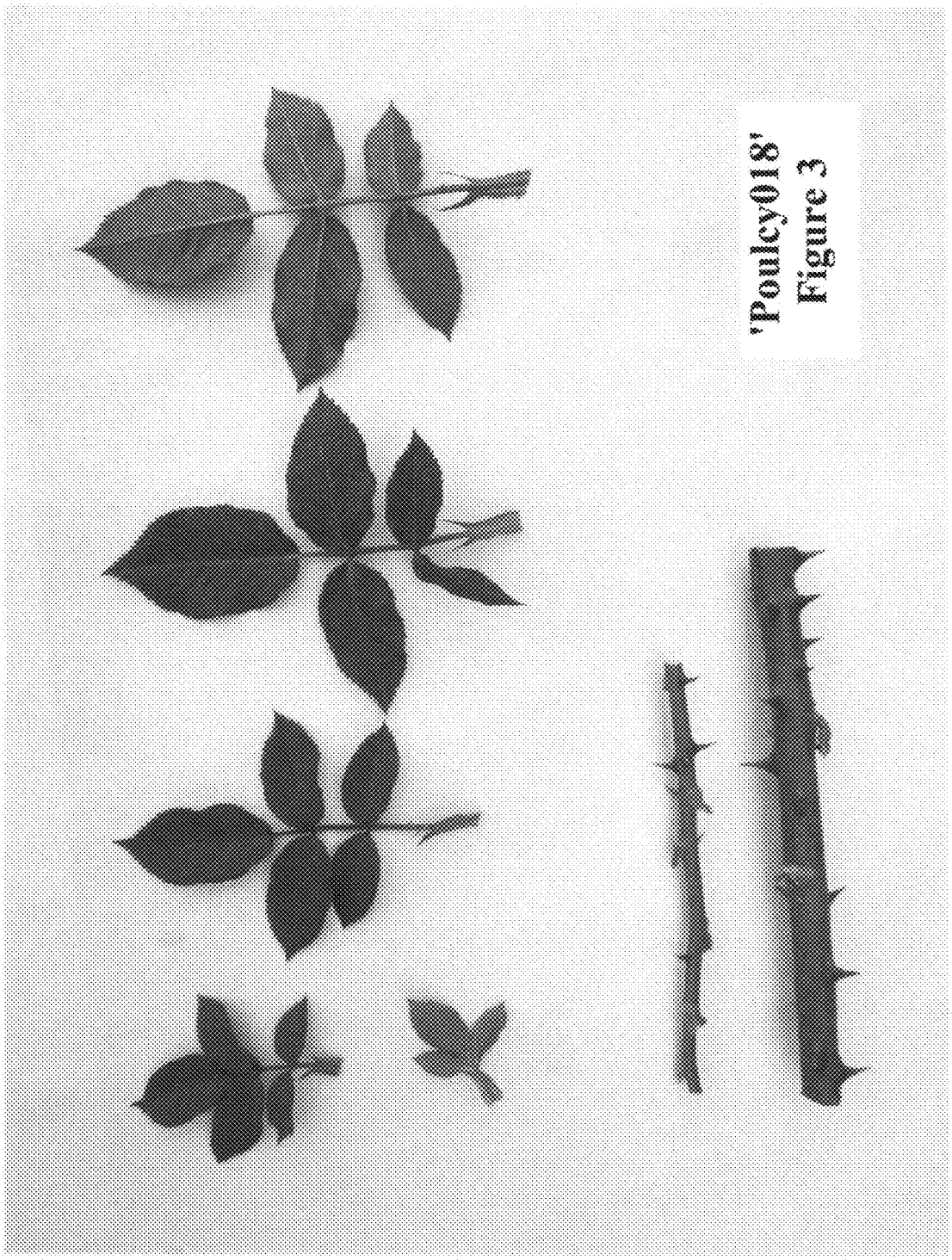
FIG. 3; Leaves and stems.
Figure 4:
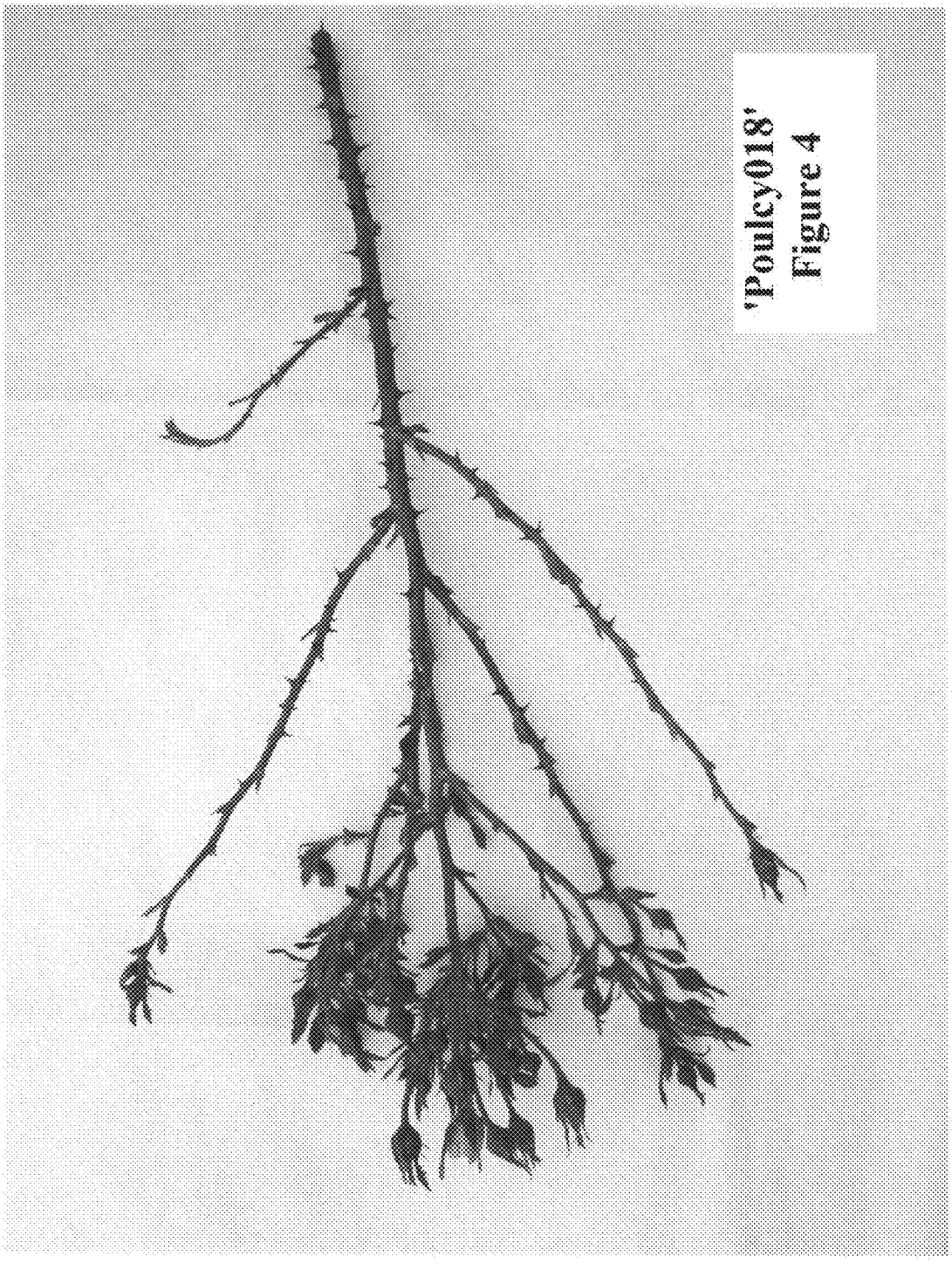
FIG. 4; Flowering branch.

The following is a description of 'Poulcy018', as observed in its growth in in a field nursery in Benton County, Oreg. Observed plants are 3 years of age, and were grown on their own root systems. Color references are made using The Royal Horticultural Society (London, England) Colour Chart, 2001, except where common terms of color are used.

For a comparison, several physical characteristics of the rose variety 'Poulymp', U.S. Plant Pat. No. 16,744 are compared to 'Poulcy018' in Chart 1.

CHART 1

| | 'Poulcy018' | 'Poulymp' |
|---|---|---|
| Petal Count | 40 | 25 to 30 |
| Flower Diameter | 55 to 60 mm | 60 to 70 mm |
| General Tonality of Flower Color | Yellow Group 13A and Orange Group 29A | Yellow-Orange Group 20B, Orange Group 24C, and Yellow-Orange Group 21C |

FLOWER AND FLOWER BUD

Blooming habit: Stages of continuous periods of bloom, beginning mid-May ending at the time of first frost.

Flower bud:

*Size.*—Upon opening, 20 mm in length from base of receptacle to end of bud. Bud diameter is 13 mm.

*Bud form.*—Urceolate.

*Bud color.*—As sepals unfold, petals are Orange Group 25B and Yellow Group 13C. Surface: Smooth.

*Sepal inner surface.*—Color: Green Group 138A with anthocyanin Greyed-Red Group 180B. Texture: Smooth and moderately pubescent.

*Sepal outer surface.*—Color: Yellow-Green Group 144A with anthocyanic pigments the color of Greyed-Red Group 180A. Texture: Smooth.

*Sepal shape.*—Apex: Cirrhose. Base: Flat at union with receptacle.

*Sepal margin.*—Margins have medium foliaceous appendages on three of the five sepals.

*Sepal size.*—25 mm long by 10 mm wide.

*Receptacle.*—Texture: Smooth. Shape: Funnel shaped. Size: 5 mm in height by 10 mm wide. Color: Yellow-Green Group 144A.

*Peduncle.*—Surface: Smooth. Length: Range from 10 to 2 cm. Diameter: 4 to 2.5 mm. Color: Yellow-Green Group 144A with anthocyanin Greyed-Purple Group 183C.

*Pedicel.*—Surface: Smooth. Length: 20 to 25 mm. Diameter: 2 to 3 mm. Color: Yellow-Green Group 144A with anthocyanic pigments the color of Greyed-Red Group 180A. Strength: Moderate.

Flower bud development: Flower buds are borne in clusters of 5 to 9 flower buds per flowering branch resembling a panicle. Typically, flower clusters are 15 to 20 cm across, and 20 mm in height. Reduced apical dominance in flower habit causes flower buds develop in stages evenly from the base of the plant to the upper branches.

Flower bloom:

*Fragrance.*—Light floral scent.

*Duration.*—The blooms have a duration on the plant of approximately 10 days. Petals do not fall cleanly away from plant after flowers have fully matured.

*Size.*—Flower diameter is 55 to 60 mm when open. Flower depth is 25 mm.

*Flower shape.*—General shape is a cupped rosette. Very double flower with many slightly overlapping petals of different sizes.

*Shape of flower, side view.*—The upper portion is flat. The lower portion is a flattened convex.

Petalage: Under normal conditions, flowers have 40 petals total, 5 of which are petaloids.

Petal color: Upon opening, outer & inner petals: Upper surface: Yellow-Orange Group 15A. Lower surface: Orange Group 25A, splashed with Yellow Group 12A radiating from the petal spot. Basal petal spots, upon opening: Upper surface: No distinctive coloration. Lower surface: Yellow Group 12A. After opening, outer & inner petals: Upper surface: Yellow Group 12A. Lower surface: Orange Group 25C splashed with Yellow Group 12A. Basal petal spots, after opening: Upper surface: No distinctive coloration. Lower surface: Yellow Group 12A.

General tonality: On open flower Yellow Group 13A and Orange Group 29A. No change in the general tonality at the end of the 7th day. Afterwards, general tonality is Yellow-Orange Group 20C.

Petals:

*Petal reflex.*—Weak.

*Margin.*—Equally, with a cleft at the petal margin and entire. Some petals have strong undulations in the margins, others are uniform.

*Shape.*—Broadly elliptic. Apex shape: Rounded. Base shape: Rounded.

*Size.*—25 mm long by 25 mm wide. Inner petals are 20 mm long by mm 15 wide.

*Texture.*—Smooth.

*Thickness.*—Average.

Petaloids:

*Quantity.*—5 on average.

*Shape.*—Irregular. Apex is rounded. Base is acute.

*Color.*—Upper surface is Yellow-Orange Group 15A. Lower surface is Orange Group 25A, splashed with Yellow Group 12A radiating from the petal spot. Basal petal spots, upon opening: Upper surface: No distinctive coloration. Lower surface: Yellow Group 12A.

*Size.*—15 mm long by 7 mm wide.

Reproductive organs:

*Pollen.*—Color: None observed.

*Anthers.*—Size: 2 mm in length. Color: Yellow Group 12A. Quantity: 75 on average.

*Filaments.*—Color: Yellow-Orange Group 15A. Length: 5 mm.

*Pistils.*—Length: 4 mm. Quantity: 55 on average.

*Stigmas.*—Inferior in location relative to the length of the filaments and the height of the anthers. Color: Greyed-Yellow Group 160B.

*Styles.*—Color: Yellow-Green Group 145C.

*Hips.*—None observed.

PLANT

Plant growth: Arching and bushy. When grown as a field grown plant on own root, the average height of the plant is 85 cm and the average width is 100 cm.

Stems:

*Color.*—Juvenile growth: Yellow-Green Group 144A. Mature growth: Yellow-Green Group 144A.

*Length.*—On average, canes are 40 cm from the base of the plant to the flowering portion.

*Diameter.*—10 mm.

*Internodes.*—On mature canes, there is an average distance of 35 mm between nodes.

*Surface texture.*—Young wood: Smooth. Older wood: Smooth.

Prickles:

*Incidence.*—8 prickles per 10 cm of stem.

*Size.*—Average length of prickles on mature stems is 10 mm.

*Shape.*—Flat at the upper portion, and concave at the lower portion.

*Color.*—Juvenile prickles: Greyed-Orange Group N170B. Mature prickles: Greyed-Purple Group 183B.

Plant foliage: Normal number of leaflets leaves in middle of the stem: 5 leaflets.

*Compound leaf.*—115 to 140 mm (l)×75 to 85 (w).

*Quantity.*—2 leaves per 10 cm of stem on average.

*Color of mature foliage.*—Upper side: Yellow-Green Group 147A. Lower side: Yellow-Green Group 146B.

*Color of juvenile foliage.*—Upper side: Yellow-Green Group 144A. Lower side: Yellow-Green Group 144B. Anthocyanin: Greyed-Purple Group 183B at the leaf margins.

Plant leaves and leaflets:

*Stipules.*—Size: 30 mm in length. Quantity: 2 per compound leaf. Shape: Linear, slightly broad based with outward extending apices. Margins: Finely serrated with many stipitate glands. Color: The upper surface is Green Group 143B.

*Petiole.*—Length: 30 to 45 mm. Diameter: 2 mm.

*Upper surface.*—Color: Yellow-Green Group 144C. Anthocyanin the color of Greyed-Red Group 181B.

*Lower surface.*—Color: Yellow-Green Group 144A. Observations: Prickles are Greyed-Red Group 181B, 4 mm on average.

*Rachis.*—Length: 40 to 45 mm. Upper surface: Color: Yellow-Green Group 144C. Anthocyanin the color of Greyed-Red Group 181B.

*Lower surface.*—Color: Yellow-Green Group 144A. Observations: Prickles are Greyed-Red Group 181B, 4 mm on average.

*Leaflet.*—Edge: Doubly serrated. Size: Average size of the terminal leaflet on normal leaves is 47 mm in length by 27 mm wide. Shape: Generally elliptical. Base: Rounded. Apex: Mucronate. Texture: Upper and lower surfaces are smooth. Thickness: Average. Arrangement: Odd pinnate. Venation: Reticulate. Glossiness: Moderately glossy.

Disease resistance: Above average resistance to powdery and downy mildew, rust, and *Botrytis* under normal growing conditions in Benton County, Oreg. Average resistance to black spot.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the climbing rose class named 'Poulcy018', substantially as illustrated and described herein, due to its abundant yellow-orange flowers, disease resistance, and extended period of bloom.

* * * * *

'Poulcy018'

'Poulcy018'

'Poulcy018'

'Poulcy018'